(12) United States Patent
Viksoe-Nielsen et al.

(10) Patent No.: US 8,119,384 B2
(45) Date of Patent: Feb. 21, 2012

(54) PROCESS FOR PRODUCING A STARCH HYDROLYZATE

(75) Inventors: Anders Viksoe-Nielsen, Slangerup (DK); Jim Liu, Raleigh, NC (US); Carsten Andersen, Vaerloese (DK)

(73) Assignees: Novozymes A/S, Bagsvaerd (DK); Novozymes North America, Inc., Franklinton, NC (US)

( * ) Notice: Subject to any disclaimer, the term of this patent is extended or adjusted under 35 U.S.C. 154(b) by 735 days.

(21) Appl. No.: 11/763,498

(22) Filed: Jun. 15, 2007

(65) Prior Publication Data

US 2008/0009049 A1 Jan. 10, 2008

Related U.S. Application Data

(60) Provisional application No. 60/813,941, filed on Jun. 15, 2006.

(51) Int. Cl.
*C12N 9/28* (2006.01)
*C12N 9/26* (2006.01)
*C12N 9/30* (2006.01)
*C12N 9/34* (2006.01)

(52) U.S. Cl. ......... 435/202; 435/201; 435/203; 435/205

(58) Field of Classification Search .................. 435/69.1, 435/105, 161, 162, 202, 205, 320.1, 252.3; 536/23.2
See application file for complete search history.

(56) References Cited

U.S. PATENT DOCUMENTS

| 4,316,956 A | 2/1982 | Lutzen |
| 2006/0148054 A1 | 7/2006 | Fukuyama et al. |

FOREIGN PATENT DOCUMENTS

| WO | WO 2004/113551 | 12/2004 |
| WO | WO 2005/003311 | 1/2005 |
| WO | WO 2005/069840 | 8/2005 |
| WO | WO 2006/066596 | 6/2006 |

OTHER PUBLICATIONS

Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Seffernick et al. Melamine deaminase and atrazine chlorohydrolase: 98 percent identical but functionally different, J Bacteriol. Apr. 2001;183(8):2405-10.*
Anders Viksoe-Nielsen, Biocatalysis and Biotransformation, vol. 24(1/2), pp. 121-127 (2006).

* cited by examiner

*Primary Examiner* — Robert Mondesi
*Assistant Examiner* — Iqbal H Chowdhury
(74) *Attorney, Agent, or Firm* — Elias Lambiris

(57) ABSTRACT

The present invention relates to processes for producing a starch hydrolyzate and optionally a fermentation product, such as ethanol.

13 Claims, No Drawings

PROCESS FOR PRODUCING A STARCH HYDROLYZATE

CROSS-REFERENCE TO RELATED APPLICATIONS

This applications claims priority or the benefit of U.S. provisional application No. 60/813,941 filed Jun. 15, 2006, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to an improved process for production of a starch hydrolyzate, e.g., for use in a fermentation process.

BACKGROUND OF THE INVENTION

The present invention relates to processes for production of a fermentation product from milled starch-containing material, such as granular starch, at a temperature below the initial gelatinization temperature of the milled starch-containing material.

Grains, cereals or tubers of plants contain starch. The starch is in the form of microscopic granules, which are insoluble in water at room temperature. When an aqueous starch slurry is heated, the granules swell and eventually burst, dispersing the starch molecules into the solution. During this "gelatinization" process, there is a dramatic increase in viscosity. Because the solids level in a typical industrial process is around 30-40%, the starch has to be thinned or "liquefied" so that it can be handled. This reduction in viscosity is generally accomplished by enzymatic degradation in a process referred to as liquefaction. During liquefaction, the long-chained starch is degraded into smaller branched and linear chains of glucose units (dextrins) by an alpha-amylase.

A conventional enzymatic liquefaction process may be carried out as a three-step hot slurry process. The slurry is heated to between 80-85° C. and thermostable alpha-amylase added to initiate liquefaction. The slurry is then jet-cooked at a temperature between 105-125° C. to complete gelatinization of the slurry, cooled to 60-95° C. and, generally, additional alpha-amylase is added to finalize hydrolysis. The liquefaction process is generally carried out at pH between 5 and 6.

During saccharification, the dextrins from the liquefaction are further hydrolyzed to produce low molecular sugars $DP_{1-3}$ that can be metabolized by a fermenting organism, such as yeast. The hydrolysis is typically accomplished using glucoamylase, alternatively or in addition to glucoamylases, alpha-glucosidases and/or acid alpha-amylases can be used. A full saccharification step typically lasts up to 72 hours, however, it is common to do a pre-saccharification of, e.g., 40-90 minutes at a temperature above 50° C., followed by a complete saccharification during fermentation in a process known as simultaneous saccharification and fermentation (SSF).

Fermentation is performed using a fermenting organism, such as yeast, which is added to the mash. Then the fermentation product is recovered. For ethanol, e.g., fuel, potable, or industrial ethanol, the fermentation is carried out, for typically 35-60 hours at a temperature of typically around 32° C. When the fermentation product is beer, the fermentation is carried out, for typically up to 8 days at a temperature of typically around 14° C.

Following fermentation, the mash may be used, e g., as a beer, or distilled to recover ethanol. The ethanol may be used as, e.g., fuel ethanol, drinking ethanol, and/or industrial ethanol.

It will be apparent from the above discussion that the starch hydrolysis in a conventional process is very energy consuming due to the different temperature requirements during the various steps. Several patent applications address the issue by providing processes for converting granular starch into ethanol without the energy consuming gelatinisation step.

U.S. Pat. No. 4,316,956 and WO 2004/113551 provide fermentation processes for conversion of granular starch into ethanol.

The applications WO 2005/003311 and PCT/US05/46725 provide fungal alpha-amylases useful for conversion of granular starch into fermentable sugars, e.g., for ethanol production.

The application PCT/DK2005/000819 provides bacterial alpha-amylases useful for conversion of granular starch into fermentable sugars, e.g., for ethanol production.

The object of the present invention is to provide improved processes for conversion of milled starch-containing material, such as granular starch.

SUMMARY OF THE INVENTION

The present invention provides processes for producing a starch hydrolyzate from starch-containing material without gelatinization of said starch-containing material. The starch hydrolyzate may be used, e.g., as a sweetener or in the production of a fermentation product, such as ethanol. Surprisingly the inventors have discovered that by combining the action of a bacterial alpha-amylase comprising a carbohydrate-binding module and the action of a fungal alpha-amylase comprising a carbohydrate-binding module an increase in yield is achieved compared to using an increased amount of either a bacterial alpha-amylase comprising a carbohydrate-binding module or an increased amount of a fungal alpha-amylase comprising a carbohydrate-binding module.

Accordingly in a first aspect, the invention provides a process comprising saccharification of a granular starch with: a) a glucoamylase, b) a bacterial alpha-amylase comprising a carbohydrate-binding module (CBM), and, c) a fungal alpha-amylase comprising a CBM, to produce a starch hydrolyzate.

In a preferred embodiment the starch hydrolyzate of the first aspect is further contacted with a fermenting organism to produce a fermentation product, preferably ethanol. Preferably saccharification and fermentation is carried out simultaneously.

In a second aspect, the invention provides compositions of a bacterial alpha-amylase comprising a carbohydrate-binding module and the action of a fungal alpha-amylase comprising a carbohydrate-binding module. In a preferred embodiment the composition furthermore comprises a glucoamylase. Preferably the ratio between fungal acid alpha-amylase activity (AFAU) per glucoamylase activity (AGU) (AFAU per AGU) is at least 0.1, in particular at least 0.16, such as in the range from 0.12 to 0.50 or even higher.

DETAILED DESCRIPTION OF THE INVENTION

Before saccharification a slurry of starch-containing material, such as granular starch, having 20-55 weight % dry solids, preferably 25-40 weight % dry solids, more preferably 30-35% dry solids of starch-containing material is be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place high levels of stillage may be used if desired. In an embodiment the aqueous slurry contains from about 1 to about 70 vol. % stillage, preferably 15-60% vol. % stillage, especially from about 30 to 50 vol. % stillage.

In order to expose more surface of the starch-containing material it is milled. In an embodiment the particle size is between 0.05-3.0 mm, or at least 30% of the milled starch-containing material fit through a sieve with a 0.05 to 3.0 mm screen. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material or of the starch of the starch-containing material is converted into a soluble starch hydrolyzate.

The process of the invention is conducted at a temperature below the initial gelatinization temperature. In a preferred embodiment, the process is carried out as a simultaneous saccharification and fermentation process. In such preferred embodiment the process is typically carried out at a temperature between 28° C. and 36° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as the glucose level, is kept at a low level such as below about 3 wt. %, preferably below about 2 wt. %, more preferred below about 1 wt. %., even more preferred below about 0.5%, or even more preferred below about 0.1 wt. %. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt. % or below about 0.2 wt. %.

The process of the invention may be carried out at a pH in the range between 3 and 7, preferably from 3.5 to 6, or more preferably from 4 to 5.

Any suitable starch-containing starting material comprising granular starch may be used according to the present invention. Examples of starch-containing starting materials, suitable for use in the processes of present invention, include tubers, roots, stems, whole grains, corns, cobs, wheat, barley, rye, milo, sago, cassava, tapioca, sorghum, rice peas, beans, or cereals, sugar-containing raw materials, such as molasses, fruit materials, sugar, cane or sugar beet, potatoes, and cellulose-containing materials, such as wood or plant residues. Contemplated are both waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch-containing material comprising milled whole grain including non-starch fractions such as germ residues and fibers.

The starch-containing raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolyzate is used in production of syrups. Both dry and wet milling is well known in the art of starch processing and is equally contemplated for the process of the invention. In an embodiment the particle size after milling is between 0.05 to 3.0 mm, or so that at least 30%, preferably at least 50%, more preferably at least 70%, even more preferably at least 90% of the milled starch-containing material fit through a sieve with a 0.05 to 3.0 mm screen, and preferably with a 0.1~0.5 mm screen.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein and Lii, 1992, Starch/Stärke, 44(12): 461-466.

The term "starch hydrolyzate" is understood as the soluble degradation products of the hydrolysis processes of the invention. The starch hydrolysis may comprise mono-, di-, and oligosaccharides, such as glucose, maltose, maltodextrins, cyclodextrins and any mixture of these. Preferably at least 90%, at least 91%, at least 92%, at least 93%, at least 94%, at least 95%, at least 96%, at least 97% or at least 98% of the dry solids of the granular starch is converted into a soluble starch hydrolyzate.

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, as are well known in the art. Preferred fermentation processes are anaerobic fermentation processes, as are well known in the art.

The term "Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of the *Saccharomyces* spp., and in particular, *Saccharomyces cerevisiae*. Commercially available yeast include, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Fungal and Bacterial Alpha-Amylase Comprising a CBM

According to the invention a fungal alpha-amylase comprising a CBM and a bacterial alpha-amylase comprising a CBM are applied in the process of the invention. In a preferred embodiment the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases Comprising a CBM

By the term a "bacterial alpha-amylase comprising a CBM" is understood an enzyme comprising a catalytic domain and a CBM, said catalytic domain and said CBM both derived from a bacterial source. The bacterial alpha-amylase comprising a CBM may be a wild-type bacterial enzyme, a variant of such a wild-type bacterial enzyme, or a hybrid enzyme comprising a bacterial alpha-amylase catalytic domain and a bacterial CBM. In a preferred embodiment of the invention the bacterial alpha-amylase catalytic domain and/or bacterial CBM is derived from the genus *Bacillus* or the genus *Anoxybacillus*.

Preferred for the invention is any bacterial alpha-amylase comprising a CBM, both hybrids and wild-types, wherein the CBM has the sequence shown as amino acids 521~619 in SEQ ID NO: 1 herein or the CBM has a sequence homologous to said sequence.

Also preferred for the invention is any bacterial alpha-amylase comprising a CBM, both hybrids and wild-types, Wherein the catalytic domain has the sequence shown as amino acids 32-520 in SEQ ID NO: 1 herein or the catalytic domain has a sequence homologous to said sequence.

In another preferred embodiment the bacterial alpha-amylase comprising a CBM comprises a catalytic domain derived from a strain of *B. licheniformis*, *B. amyloliquefaciens*, *B. subtilis* or *B. stearothermophilus*, but may also be derived from other *Bacillus* sp. Specific examples of contemplated alpha-amylase catalytic domains include a amylase catalytic domain having at least 60%, at least 70%, at least 80% or even at least 90% identity to the amylase from *Bacillus licheniformis* (BLA) shown in SEQ ID NO: 35, the *B. licheniformis* variant LE429 shown in SEQ ID NO: 41, the amylase from *B. stearothermophilus* (BSG) shown in SEQ ID NO: 36, the amylase from *B. amyloliquefaciens* (BAN) shown in SEQ ID NO: 37, the amylase from *B. halodurance* SP722 shown in SEQ ID NO: 38, the amylase SP690 shown in SEQ ID NO: 39, the amylase AA560 shown in SEQ ID NO: 40 in patent application PCT/DK2005/000819 (hereby incorporated by reference). The catalytic domain may also be derived from an amylase from *Pseudomonas saccharophilia*, such as from the amylase disclosed as SEQ ID NO: 1 in WO 04/111217 (hereby incorporated by reference).

In an embodiment of the invention the bacterial alpha-amylase comprising a CBM is an enzyme comprising a catalytic domain having a degree of identity of at least 70%, preferably at least 80%, more preferred at least 85%, even more preferred at least 90%, such as at least 95%, at least 96%, at least 97%, at least 98% or at least 99% identity to any of the sequences shown in SEQ ID NO: 1, 2 or 3 in WO 99/19467 (hereby incorporated by reference). The *Bacillus* alpha-amylase catalytic domain may also be a variant and/or hybrid sequence, especially one described in any of WO 96/23873, WO 96/23874, WO 97/41213, WO 99/19467, WO 00/60059, and WO 02/10355 (all of which are hereby incorporated by reference). Specifically contemplated alpha-amylase variants are disclosed in U.S. Pat. Nos. 6,093,562, 6,187,576, and 6,297,038 (all of which are hereby incorporated by reference) and include *Bacillus stearothermophilus* alpha-amylase (BSG alpha-amylase) variants having a double deletion disclosed in WO 96/23873—see e.g., page 20, lines 1-10 (hereby incorporated by reference), preferably corresponding to delta(181-182) compared to the wild-type BSG alpha-amylase amino acid sequence set forth in SEQ ID NO: 7 disclosed in WO 99/19467 (hereby incorporated by reference). Even more preferred are *Bacillus* alpha-amylase catalytic domains, especially *Bacillus stearothermophilus* alpha-amylase, which have a double deletion corresponding to delta (181-182) and further comprise a N193F substitution (also denoted I181*+G182*+N193F) compared to the wild-type BSG alpha-amylase amino acid sequence set forth in SEQ ID NO: 3 disclosed in WO 99/19467.

In a particularly preferred embodiment the bacterial alpha-amylase comprising a CBM is a wild-type bacterial alpha-amylase derived from a strain of *Anoxybacillus contaminans*. Preferably the bacterial alpha-amylase comprising a CBM has the sequence shown in SEQ ID NO: 1 herein. Also preferred are polypeptides having at least 70% identity, such as at least 80% or even at least 90% identity, such as at least 95%, at least 96%, at least 97%, at least 98%, or at least 99% identity to SEQ ID NO: 1 herein. In another embodiment the bacterial alpha-amylase comprising a CBM is one of the hybrid enzymes disclosed in PCT/DK2005/000819 as SEQ ID NO: 4, SEQ ID NO: 6, SEQ ID NO: 8, SEQ ID NO: 10, SEQ ID NO: 12, SEQ ID NO: 14 (hereby incorporated by reference) or an amino acid sequence homologous to any of these sequences.

The bacterial alpha-amylase may be used in an amount of 0.001 to 1.0 mg/g DS, preferably in an amount of 0.01 to 0.5 mg/g DS, more preferably in an amount of 0.02 to 0.2 mg/g DS. Measured in AFAU the bacterial alpha-amylase may be used in an amount of 0.01-10 AFAU/g of DS, in an amount of 0.05-2.5 AFAU/g of DS, or more preferably in an amount of 0.1-1 AFAU/g of DS, such as approximately 0.5 AFAU/g DS.

Measured in KNU the bacterial alpha-amylase may be used in an amount of 0.001-10 KNU/g of DS, in an amount of 0.005-2 KNU/g of DS, or more preferably in an amount of 0.01-0.2 KNU/g of DS, such as approximately 0.035 KNU/g DS.

Fungal Alpha-Amylases Comprising a CBM

By the term a "fungal alpha-amylase comprising a CBM" is understood an enzyme comprising a catalytic domain and a CBM, said catalytic domain and said CBM both derived from a fungal source. The fungal alpha-amylase comprising a CBM may be a wild-type fungal enzyme, a variant of such a wild-type fungal enzyme, or a hybrid enzyme comprising a fungal alpha-amylase catalytic domain and a fungal CBM.

In an embodiment the wild-type acid alpha-amylase is derived from a strain of *Aspergillus kawachi*, in particular the polypeptide shown in SEQ ID NO: 41 in WO 2005/003311 or homologous sequences, e.g., variants of said polypeptide comprising one or more of the substitutions G33A, I36K, S74A, D75Y, E77D, P120A, I153D, D154N, W155Y, D156E, N157D, L158Q, Q162E, E166L, T169N, I170T, E199K, E199L, D232L, N233D, N235D, L238Y, D239T, W256Y, Q257P, E331Q, S336A, D339K, D339N, V340D, and Y342A. The most preferred variants comprise one or more of the following substitutions; S74A, E166L, E199L, D339K, and D156E. Yet more preferred is the variant having the multiple substitutions S74A/E166L/E199L.

In a preferred embodiment the fungal alpha-amylase comprising a CBM is a hybrid alpha-amylase. Fungal hybrid enzymes, as referred to herein, include species comprising an amino acid sequence of an alpha-amylase enzyme (EC 3.2.1.1) of fungal origin linked (i.e., covalently bound) to an amino acid sequence comprising a carbohydrate-binding module (CBM), preferably of fungal origin.

Fungal alpha-amylases catalytic domains suitable for use in a hybrid enzyme for use in the process of the invention include acid alpha-amylases derived from a strain of the genus *Aspergillus*, such as, *Aspergillus oryzae* and *Aspergillus niger* alpha-amylases. A preferred fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e., at least 70%, at least 75%, at least 80%, at least 85% at least 90%, at least 95%, at least 96%, at least 97%, at least 98%, at least 99% or even 100% identity to the mature part of the amino acid sequence shown in SEQ ID NO: 10 in WO 96/23874. A preferred hybrid enzyme comprises a Fungamyl-like alpha-amylase catalytic domain and a CBM derived from the *A. rolfsii* glucoamylase.

Another preferred acid alpha-amylase catalytic domain suitable for use in a hybrid enzyme for use in the process of the invention is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 8 in WO 2005/003311. Preferred acid alpha-amylase amylases catalytic domains also comprise variants of said acid fungal amylase having at least 70% identity, such as at least 80% or at least 90% identity, such as at least 95%, at least 96%, at least 97%, at least 98%, or even at least 99% identity to SEQ ID NO: 8 in WO 2005/003311. Preferably the fungal alpha-amylase comprising a COM is the variant JA01 disclosed in WO 2005/003311.

Another preferred acid alpha-amylase amylases catalytic domains suitable for use in a hybrid enzyme for use in the process of the invention is any alpha-amylase catalytic domain disclosed in patent application PCT/US05/46725 (hereby incorporated by reference), and preferably the catalytic domain is derived from any species disclosed therein, and in particular selected from the group consisting of *Thermomyces lanuginosus*; in particular a polypeptide having the amino acids 1-441 in SEQ ID NO: 14, *Malbranchea* sp.; in particular a polypeptide having the amino acids 1-471 in SEQ ID NO: 18, *Rhizomucor pusillus*; in particular a polypeptide having the amino acids 1-450 in SEQ ID NO: 20, *Dichotomocladium hesseltinei*; in particular a polypeptide having the amino acids 1-445 in SEQ ID NO: 22, *Stereum* sp.; in particular a polypeptide having the amino acids 1-498 in SEQ ID NO: 26, *Trametes* sp.; in particular a polypeptide having the amino acids 18-513 in SEQ ID NO: 28, *Coriolus consors*, in particular a polypeptide having the amino acids 1-507 in SEQ ID NO: 30, *Dinemasporium* sp.; in particular a polypeptide having the amino acids 1-481 in SEQ ID NO: 32, *Cryptosporiopsis* sp.; in particular a polypeptide having the amino acids 1-495 in SEQ ID NO: 34, *Diplodia* sp., in particular a polypeptide having the amino acids 1-477 in SEQ ID NO: 38, *Gliocladium* sp.; in particular a polypeptide having the amino acids 1-449 in SEQ ID NO: 42, *Nectria* sp.; in particular a polypeptide having the amino acids 1-442 in SEQ ID NO: 115, *Fusarium* sp.; in particular a polypeptide having the amino acids 1-480 in SEQ ID NO: 4, a polypeptide having the amino acids 1-478 in SEQ ID NO: 6, or a polypeptide having the amino acids 1-441 in SEQ ID NO: 117, *Thermoascus aurantiacus*; in particular a polypeptide having the amino acids 1-477 in SEQ ID NO: 125, *Thamindium elegans*; particular a polypeptide having the amino acids 1-446 in SEQ ID NO: 131, *Absidia cristata*; in particular a polypeptide having the amino acids 41-481 in SEQ ID NO: 157, *Acremonium* sp,; in particular a polypeptide having the amino acids 22-626 in SEQ ID NO: 159, *Coniochaeta* sp.; in particular a polypeptide having the amino acids 24-630 in SEQ ID NO: 161, *Meńpilus giganteus*, in particular a polypeptide having the amino acids 27-602 in SEQ ID NO: 163, *Penicillium* sp.; in particular a polypeptide having the amino acids 21-643 in SEQ ID NO: 165, *Streptomyces limosus*; in particular a polypeptide having the amino acids 29-566 in SEQ ID NO: 167, *Subulispora procurvata*; in particular a polypeptide having the amino acids 22-613 in SEQ ID NO: 169, *Syncephalastrum racemosum*; in particular a polypeptide having the amino acids 21-463 in SEQ ID NO: 171, *Trametes currugata*; in particular a polypeptide having the amino acids 21-587 in SEQ ID NO: 173, *Trichophaea saccata*; in particular a polypeptide having the amino acids 30-773 in SEQ ID NO: 175, *Valsańa rubricosa*, in particular a polypeptide having the amino acids 22-586 in SEQ ID NO: 177 and *Valsaria spartii*; in particular a polypeptide having the amino acids 20-582 in SEQ ID NO: 179 in PCT/US05/46725 (hereby incorporated by reference). Also preferred are alpha-amylase amylases catalytic domains having a sequence homologous to the aforementioned polypeptides.

Most preferably a hybrid comprises a CBM disclosed in patent application PCT/US05/46725 (hereby incorporated by reference), preferably the CBM is from a glucoamylase selected from the group consisting of the *Pachykytospora papayracea* (SEQ ID NO: 76), *Trametes cingulata* (SEQ ID NO: 78), *Leucopaxillus gigantus* (SEQ ID NO: 80), *Athelia rolfsii* (SEQ ID NO: 92), *Aspergillus kawachii* (SEQ ID NO: 94), *Aspergillus niger* (SEQ ID NO: 96) or from a alpha-amylase selected from the group consisting of *Trichopheraea saccata* (SEQ ID NO: 52), *Subulispora provurvata* (SEQ ID NO: 82), *Valsaria rubricosa* (SEQ ID NO: 84), *Acremonium* sp. (SEQ ID NO: 86), *Meripilus giganteus* (SEQ ID NO: 88), *Bacillus flavothermus* (*Anoxybacillus contaminans*) (SEQ ID NO: 90), *Coniochaeta* sp. (SEQ ID NO: 98), *Coniochaeta* sp. (SEQ ID NO: 137), *Trametes corrugate* (SEQ ID NO: 139), *Valsario spartii* (SEQ ID NO: 141) and *Penicillium* sp. (SEQ ID NO: 143) in PCT/US05/46725 (hereby incorporated by reference). Also preferred are sequences homologous to any of the aforementioned sequences.

Also preferred for the invention are any of the polypeptides V001, V002, V003, V004, V005, V006, V007, V008, V009, V010, V011, V012, V013, V014, V015, V016, V017, V018, V019, V021, V022, V023, V024, V025, V026, V027, V028, V029, V030, V031, V032, V033, V034, V035, V036, V037, V038, V039, V040, V041, V042, V043, V047, V048, V049, V050, V051, V052, V054, V055, V057, V059, V060, V061, V063, V064, V065, V066, V067, V068 and V069 disclosed in patent application PCT/US05/46725 and hereby incorporated by reference. Also preferred are sequences homologous to any of the aforementioned sequences.

More preferred are a fungal alpha-amylase comprising a CBM wherein the fungal alpha-amylase catalytic domain is an amino acid sequence having at least 70% homology to amino acids 13 to 450 of SEQ ID NO: 4, preferably derived from *Rhizomucor pusillus* and/or the fungal CBM is an amino acid sequence having at least 70% homology to amino acids 488 to 595 in SEQ ID NO: 2, preferably a sequence derived from a strain of *Aspergillus niger*, preferably a sequence derived from *Aspergillus niger* glucoamylase.

Most preferably the fungal alpha-amylase comprising a CBM is the hybrid V039 disclosed in PCT/US05/46725 comprising the CD from *Rhizomucor pusillus* alpha-amylase and the CBM and linker from *Aspergillus niger* glucoamylase and having the sequence shown as amino acids 13-595 in SEQ ID NO: 2 herein.

The fungal alpha-amylase may be used in amounts of 0.001 to 1.0 mg/g DS, preferably in an amount of 0.01 to 0.5 mg/g DS, more preferably in an amount of 0.02 to 0.2 mg/g DS. Measured in AFAU the fungal alpha-amylase may be used in an amount of 0.01-10 AFAU/g of DS, in an amount of 0.05-2.5 AFAU/g of DS, or more preferably in an amount of 0.1-1 AFAU/g of DS, such as approximately 0.5 AFAU/g DS.

Glucoamylase

The term "glucoamylase activity" means a glucan 1,4-alpha-glucosidase which hydrolyzes the terminal 1,4-linked alpha-D-glucose residues successively from non-reducing ends of the chains with release of beta-D-glucose belonging to the Enzyme Class EC 3.2.1.3.

The glucoamylase used in a process of the invention may have the amino acid sequence disclosed in SEQ ID NO: 2 in PCT/US05/46724, and shown herein as SEQ ID NO: 3 or an amino acid sequence that is at least 70%, preferably at least 75%, or at least 80%, or at least 85%, or 90%, or at least 95%, at least 96%, at least 97%, at least 98% or even at least 99% identical to SEQ ID NO: 3. The glucoamylase preferably is derived from *Trametes cingulata*.

Alternatively the glucoamylase used in a process of the invention may have the amino acid sequence shown PCT/US05/01147 as amino acid residues 1 to 561 in SEQ ID NO: 2, or an amino acid sequence that is at least 70%, preferably at least 75%, or at least 80%, or at least 85%, or 90%, or at least 95%, at least 96%, at least 97%, at least 98% or even at least 99% identical to said SEQ ID NO: 2 (amino acid residues 1 to 561). The glucoamylase preferably is derived from *Athelia rolfsii*.

Also preferred are the glucoamylase derived from *Talaromyces emersonii* disclosed in WO 99/28448 and the glucoamylase derived from *Aspergillus niger* disclosed in Boel et al. (1984), EMBO J. 3(5): 1097-1102. *Aspergillus niger* glucoamylase is available from Novozymes A/S as Sprizyme Plus™ and Sprizyme Fuel™.

The glucoamylase may be used in an amount of 0.01 to 2.0 mg/g DS, preferably in an amount of 0.05 to 1.0 mg/g DS, more preferably in an amount 0.1 to 0.5 mg/g DS. Measured in AGU the glucoamylase may be used in an amount of 0.01-10 AGU/g of DS, in an amount of 0.05-2.5 AGU/g of DS, or more preferably in an amount of 0.1-1 AGU/g of DS, such as approximately 0.5 AGU/g DS.

Protease

According to the process of the invention a protease may be present during saccharification and/or fermentation.

In a preferred embodiment the protease is an acid protease of microbial origin, preferably of fungal or bacterial origin.

Suitable proteases include microbial proteases, such as fungal and bacterial proteases. Preferred proteases are acidic proteases, i.e., proteases characterized by the ability to hydrolyze proteins under acidic conditions below pH 7, preferably from 3.5 to 6, or more preferably from 4 to 5.

Contemplated acid fungal proteases include fungal proteases derived from *Aspergillus*, *Mucor*, *Rhizopus*, *Candida*, *Coriolus*, *Endothia*, *Enthomophtra*, *Irpex*, *Penicillium*, *Sclerotium* and *Torulopsis*. Especially contemplated are proteases derived from *Aspergillus niger* (see, e.g., Koaze et al., 1964, Agr. Biol. Chem. Japan, 28: 216), *Aspergillus saitoi* (see. e.g., Yoshida, 1954, J. Agr. Chem. Soc. Japan, 28: 66), *Aspergillus awamori* (Hayashida et al., 1977, Agric. Biol. Chem., 42(5): 927-933, *Aspergillus aculeatus* (WO 95/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832. Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the proteases having at least 90% identity to amino acid sequence disclosed as SEQ. ID. NO: 1 in the WO 2003/048353 such as at least 92%, at least 95%, at least 96%, at least 97%, at least 98%, or particularly at least 99% identity.

Also contemplated are papain-like proteases such as proteases within E.C. 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

Proteases may be added in the amounts of 0.1-1000 AU/kg dm, preferably 1-100 AU/kg DS and most preferably 5-25 AU/kg DS.

Additional Ingredients

Additional ingredients may be present during saccharification and/or fermentation to increase the effectiveness of the process of the invention. For instance, nutrients (e.g., fermentation organism micronutrients), antibiotics, salts (e.g., zinc or magnesium salts), other enzymes such as phytase, cellulase, hemicellulase, exo and endoglucanase, and xylanases.

Recovery of Fermentation Product

The fermentation product, such as ethanol, may optionally be recovered after fermentation. The recovery may be performed by any conventional manner such as, erg., distillation.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

Materials and Methods

Glucoamylases:

Acid bacterial alpha-amylase (ABAA) derived from *Anoxybacillus contaminans* and having the sequence shown in SEQ ID NO: 1.

Acid fungal alpha-amylase (AFAA) comprising the *Rhizomucor pusillus* alpha-amylase catalytic domain and the *Aspergillus niger* glucoamylase linker and CBM and having the sequence shown in SEQ ID NO: 2.

Glucoamylase derived from *Aspergillus niger* disclosed in Boel et al., 1984, EMBO J., 3(5): 1097-1102 and available from Novozymes A/S.

Glucoamylase derived from *Trametes cingulata* and having the sequence shown in SEQ ID NO: 3.

Yeast: Red Star™ available from Red Star/Lesaffre, USA

Homology/Identity

In context of the present invention polypeptide "identity" means the degree of identity between two amino acid sequences. The identity may suitably be determined by computer programs known in the art, such as, GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., 1970, Journal of Molecular Biology, 48: 443-453. The following settings for polypeptide sequence comparison are used: GAP creation penalty of 3.0 and GAP extension penalty of 0.1. The term "homologous sequence" is used to characterize a sequence having an amino acid sequence that is at least 70%, preferably at least 75%, or at least 80%, or at least 85%, or 90%, or at least 95%, at least 96%, at least 97%, at least 98% or even at least 99% identical to a known sequence. The relevant part of the amino acid sequence for the homology determination is the mature polypeptide, i.e., without the signal peptide.

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby incorporated by reference.

Acid Alpha-Amylase Activity

When used according to the present invention the activity of any acid alpha-amylase may be measured in AFAU (Acid Fungal Alpha-amylase Units). Alternatively activity of acid alpha-amylase may be measured in AAU (Acid Alpha-amylase Units).

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard conditions/reaction conditions:

| | |
|---|---|
| Substrate: | Soluble starch. Concentration approx. 20 g DS/L. |
| Buffer: | Citrate, approx. 0.13 M, pH = 4.2 |
| Iodine solution: | 40.176 g potassium iodide + 0.088 g iodine/L |
| City water: | 15°-20°dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in European Patent No. 140410, which disclosure is hereby incorporated by reference.

Acid Alpha-Amylase Activity (AFAU)

Acid alpha-amylase activity may be measured in AFAU (Acid Fungal Alpha-amylase Units), which are determined relative to an enzyme standard. 1 FAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

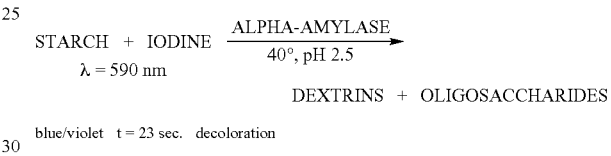

blue/violet t = 23 sec. decoloration

Standard conditions/reaction conditions:

| | |
|---|---|
| Substrate: | Soluble starch, approx. 0.17 g/L |
| Buffer: | Citrate, approx. 0.03 M |
| Iodine (I2): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby incorporated by reference.

Glucoamylase Activity

Glucoamylase activity may be measured in AGI units or in AmyloGlucosidase Units (AGU).

Glucoamylase-Activity (AGI)

Glucoamylase (equivalent to amyloglucosidase) converts starch into glucose. The amount of glucose is determined here by the glucose oxidase method for the activity determination. The method described in the section 76-11 Starch-Glucoamylase Method with Subsequent Measurement of Glucose with Glucose Oxidase in "Approved methods of the American Association of Cereal Chemists". Vol. 1-2 AACC, from American Association of Cereal Chemists, 2000; ISBN: 1-891127-12-8.

One glucoamylase unit (AGI) is the quantity of enzyme which will form 1 micromol of glucose per minute under the standard conditions of the method.

| Standard conditions/reaction conditions: | |
|---|---|
| Substrate: | Soluble starch, concentration approx. 16 g dry matter/L. |
| Buffer: | Acetate, approx. 0.04 M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH ~9) |
| Enzyme concentration: | 0.15-0.55 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |
| Color reaction: | |
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby incorporated by reference.

Proteolytic Activity (AU)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milliequivalent of tyrosine.

A folder AF 4/5 describing the analytical method in more detail is available upon request to Novozymes A/S, Denmark, which folder is hereby incorporated by reference.

EXAMPLE 1

A 35% DS slurry was prepared from 194.44 g ground corn (90% less than 0.5 mm), 305.56 g of 37 mM NaOAc, 0.025% sodium azide, 20 mM $CaCl_2$, pH 4.5. The pH was adjusted to 4.5 with 5N NaOH and the slurry was incubated with stirring at room temperature for one hour. For each reaction 5 g slurry was added to a 20 ml vial,—and the vials were incubated at 32° C. for one hour prior to enzyme dosing. Each vial was dosed with the appropriate amount of enzyme as shown in Table 1, capped and vortexed immediately, Vials were incubated at 32° C. and vortexed at 0.5, 1, 2, 3, and 4 hours. The reactions were stopped at 4 hours by addition of 50 micrL of 40% $H_2SO_4$. Three replicates were run for each reaction. Sample preparation consisted of centrifuging and filtering the supernatant through a 0.45 micrometer filter. Samples awaiting HPLC analysis were stored at 4° C. The HPLC results are shown in Table 1 below.

TABLE 1

Sugar concentrations in hydrolyzate after incubation with combinations of various glucoamylases (GA), bacterial alpha-amylase (BAA) and fungal alpha-amylase (FAA).

| | Enzyme Dose (mg enzyme protein/gDS) | | | Sugar Concentration (g/l) | | |
|---|---|---|---|---|---|---|
| Glucoamylase | GA dose | BAA | FAA | Glucose | maltose | Maltotriose |
| A. niger GA | 0.150 | 0.0036 | — | 33.4 | 0.87 | 0.42 |
| A. niger GA | 0.150 | 0.0073 | — | 35.2 | 0.91 | 0.46 |
| A. niger GA | 0.150 | 0.0219 | — | 38.4 | 0.99 | 0.57 |
| A. niger GA | 0.150 | 0.0657 | — | 42.6 | 1.12 | 0.79 |
| T. cingulata GA | 0.100 | 0.0036 | — | 30.4 | 1.02 | 0.44 |
| T. cingulata GA | 0.100 | 0.0073 | — | 32.4 | 1.18 | 0.50 |
| T. cingulata GA | 0.100 | 0.0219 | — | 39.7 | 2.33 | 0.84 |
| — | — | 0.0036 | 0.033 | 25.0 | 10.2 | 3.24 |
| — | — | 0.0073 | 0.033 | 25.5 | 10.8 | 3.57 |
| — | — | 0.0219 | 0.033 | 26.2 | 12.2 | 4.17 |
| — | — | 0.0657 | 0.033 | 26.5 | 13.8 | 5.07 |
| A. niger GA | 0.100 | 0.0036 | 0.033 | 44.2 | 1.91 | 0.63 |
| A. niger GA | 0.100 | 0.0073 | 0.033 | 45.1 | 2.05 | 0.69 |
| A. niger GA | 0.100 | 0.0219 | 0.033 | 47.6 | 2.24 | 0.84 |

EXAMPLE 2

Ground corn, 410 g of (90% less than 0.5 mm) was mixed 590 g tap water, 3.0 mL 1 g/L penicillin and 1 g of urea. The pH was adjusted to 4.5 with 5 N NaOH. DS level was determined to be 35%. 5 g of this slurry was added to a 20 ml vials for each reaction. Each vial was dosed with the appropriate amount of enzyme according to tables 2 or 3, followed by addition of 200 microL yeast propagate/5 g fermentation before incubation at 32° C. 9 replicate fermentations of each treatment were run. Three replicates were selected for 24 hour, 48 hour and 70 hour time point analysis. Vials were vortexed at 24, 48 and 70 hours. The time point analysis consisted of weighing the vials and prepping the sample for HPLC. The HPLC preparation consisted of stopping the reaction by addition of 50 microL of 40% $H_2SO_4$, centrifuging, and filtering through a 0.45 um filter. Samples awaiting HPLC analysis were stored at 4° C. The HPLC results are shown in table 2.

TABLE 2

Ethanol yields after incubation with yeast and combinations of *T. cingulata* glucoamylase (GA) bacterial alpha-amylase (BAA) and fungal alpha-amylase (FAA).

| Enzyme Dose (mg enzyme/g DS) | | | Ethanol Yield (% w/v) | | |
|---|---|---|---|---|---|
| *T. cingulata* GA | BAA | FAA | 24 hr | 48 hr | 70 hr |
| — | 0.000 | 0.033 | 6.82 | 10.67 | 13.16 |
| — | 0.050 | 0.033 | 7.18 | 11.55 | 13.30 |
| 0.060 | 0.000 | 0.033 | 9.13 | 14.16 | 15.18 |
| 0.060 | 0.050 | 0.033 | 9.23 | 14.31 | 16.06 |
| 0.060 | 0.000 | — | 4.45 | 6.63 | 8.54 |
| 0.060 | 0.050 | — | 5.21 | 7.51 | 9.43 |
| 0.027 | — | 0.015 | 10.87 | 14.26 | 15.32 |
| 0.054 | — | 0.030 | 9.39 | 13.38 | 15.77 |
| 0.162 | — | 0.090 | 13.05 | 15.19 | 15.58 |

The invention claimed is:

1. A process for saccharifying a granular starch, comprising treating the granular starch with:
   a) a glucoamylase,
   b) a bacterial alpha-amylase comprising a carbohydrate-binding module, and
   c) a fungal alpha-amylase comprising a carbohydrate-binding module, to produce a starch hydrolyzate.

2. The process of claim 1, further comprising contacting the starch hydrolyzate with a fermenting organism to produce a fermentation product.

3. The process of claim 2, wherein the saccharification and fermentation are carried out simultaneously.

4. The process of claim 2, further comprising recovering the fermentation product after fermentation.

5. The process of claim 4, wherein the fermentation product is an alcohol.

6. The process of claim 1, wherein the fungal alpha-amylase comprising a carbohydrate-binding module and/or the bacterial alpha-amylase comprising a carbohydrate-binding module is an acid fungal alpha-amylase and/or an acid bacterial alpha-amylase.

7. The process of claim 1, wherein the carbohydrate-binding module of the fungal alpha-amylase has an amino acid sequence of amino acids 488 to 595 in SEQ ID NO: 2.

8. The process of claim 1, wherein the fungal alpha-amylase comprising a carbohydrate-binding module has an amino acid sequence of amino acids 13 to 595 in SEQ ID NO: 2.

9. The process of claim 1, wherein the bacterial alpha-amylase comprises a catalytic domain which has an amino acid sequence having at least 90% homology to amino acids 32 to 520 in SEQ ID NO: 1.

10. The process of claim 1, wherein the bacterial alpha-amylase comprises a catalytic domain which has an amino acid sequence having at least 95% homology to amino acids 32 to 520 in SEQ ID NO: 1.

11. The process of claim 1, wherein the carbohydrate-binding module of the bacterial alpha-amylase has an amino acid sequence of amino acids 521 to 619 in SEQ ID NO: 1.

12. The process of claim 1, wherein the glucoamylase is an *Aspergillus niger*, *Athelia rolfsii*, or *Trametes cingulata* glucoamylase.

13. The process of claim 1, wherein the process is performed in the presence of a protease or a phytase.

* * * * *

SEQUENCE LISTING

<160> NUMBER OF SEQ ID NOS: 3

<210> SEQ ID NO 1
<211> LENGTH: 619
<212> TYPE: PRT
<213> ORGANISM: Anoxybacillus contaminans
<220> FEATURE:
<221> NAME/KEY: SIGNAL
<222> LOCATION: (1)..(31)
<220> FEATURE:
<221> NAME/KEY: CD
<222> LOCATION: (32)..(520)
<220> FEATURE:
<221> NAME/KEY: CBD
<222> LOCATION: (521)..(619)

<400> SEQUENCE: 1

```
Met Ser Leu Phe Lys Lys Ser Phe Pro Trp Ile Leu Ser Leu Leu Leu
1               5                   10                  15

Leu Phe Ser Phe Ile Ala Pro Phe Ser Ile Gln Thr Glu Lys Val Arg
            20                  25                  30

Ala Gly Ser Val Pro Val Asn Gly Thr Met Met Gln Tyr Phe Glu Trp
        35                  40                  45

Tyr Leu Pro Asp Asp Gly Thr Leu Trp Thr Lys Val Ala Asn Asn Ala
    50                  55                  60

Gln Ser Leu Ala Asn Leu Gly Ile Thr Ala Leu Trp Leu Pro Pro Ala
65                  70                  75                  80

Tyr Lys Gly Thr Ser Ser Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
            100                 105                 110

Gly Thr Lys Thr Gln Tyr Ile Gln Ala Ile Gln Ala Ala His Thr Ala
        115                 120                 125

Gly Met Gln Val Tyr Ala Asp Val Val Phe Asn His Lys Ala Gly Ala
    130                 135                 140

Asp Gly Thr Glu Leu Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Thr Asp Trp Asp Glu Ser Arg Lys Leu Asn Arg
        195                 200                 205

Ile Tyr Lys Phe Arg Gly Thr Gly Lys Ala Trp Asp Trp Glu Val Asp
```

```
                210                 215                 220
Thr Glu Asn Gly Asn Tyr Asp Tyr Leu Met Tyr Ala Asp Leu Asp Met
225                 230                 235                 240

Asp His Pro Glu Val Val Ser Glu Leu Lys Asn Trp Gly Lys Trp Tyr
                245                 250                 255

Val Thr Thr Thr Asn Ile Asp Gly Phe Arg Leu Asp Ala Val Lys His
                    260                 265                 270

Ile Lys Tyr Ser Phe Phe Pro Asp Trp Leu Ser Tyr Val Arg Thr Gln
                275                 280                 285

Thr Gln Lys Pro Leu Phe Ala Val Gly Glu Phe Trp Ser Tyr Asp Ile
290                 295                 300

Ser Lys Leu His Asn Tyr Ile Thr Lys Thr Asn Gly Ser Met Ser Leu
305                 310                 315                 320

Phe Asp Ala Pro Leu His Asn Asn Phe Tyr Ile Ala Ser Lys Ser Gly
                325                 330                 335

Gly Tyr Phe Asp Met Arg Thr Leu Leu Asn Asn Thr Leu Met Lys Asp
                340                 345                 350

Gln Pro Thr Leu Ala Val Thr Leu Val Asp Asn His Asp Thr Glu Pro
                355                 360                 365

Gly Gln Ser Leu Gln Ser Trp Val Glu Pro Trp Phe Lys Pro Leu Ala
370                 375                 380

Tyr Ala Phe Ile Leu Thr Arg Gln Glu Gly Tyr Pro Cys Val Phe Tyr
385                 390                 395                 400

Gly Asp Tyr Tyr Gly Ile Pro Lys Tyr Asn Ile Pro Ala Leu Lys Ser
                405                 410                 415

Lys Leu Asp Pro Leu Leu Ile Ala Arg Arg Asp Tyr Ala Tyr Gly Thr
                420                 425                 430

Gln His Asp Tyr Ile Asp Ser Ala Asp Ile Ile Gly Trp Thr Arg Glu
                435                 440                 445

Gly Val Ala Glu Lys Ala Asn Ser Gly Leu Ala Ala Leu Ile Thr Asp
                450                 455                 460

Gly Pro Gly Gly Ser Lys Trp Met Tyr Val Gly Lys Gln His Ala Gly
465                 470                 475                 480

Lys Thr Phe Tyr Asp Leu Thr Gly Asn Arg Ser Asp Thr Val Thr Ile
                485                 490                 495

Asn Ala Asp Gly Trp Gly Glu Phe Lys Val Asn Gly Gly Ser Val Ser
                500                 505                 510

Ile Trp Val Pro Lys Ile Ser Thr Ser Gln Ile Thr Phe Thr Val
                515                 520                 525

Asn Asn Ala Thr Thr Val Trp Gly Gln Asn Val Tyr Val Val Gly Asn
530                 535                 540

Ile Ser Gln Leu Gly Asn Trp Asp Pro Val His Ala Val Gln Met Thr
545                 550                 555                 560

Pro Ser Ser Tyr Pro Thr Trp Thr Val Thr Ile Pro Leu Leu Gln Gly
                565                 570                 575

Gln Asn Ile Gln Phe Lys Phe Ile Lys Lys Asp Ser Ala Gly Asn Val
                580                 585                 590

Ile Trp Glu Asp Ile Ser Asn Arg Thr Tyr Thr Val Pro Thr Ala Ala
                595                 600                 605

Ser Gly Ala Tyr Thr Ala Ser Trp Asn Val Pro
                610                 615

<210> SEQ ID NO 2
<211> LENGTH: 595
```

```
<212> TYPE: PRT
<213> ORGANISM: Artificial
<220> FEATURE:
<223> OTHER INFORMATION: hybrid protein
<220> FEATURE:
<221> NAME/KEY: SIGNAL
<222> LOCATION: (1)..(12)
<220> FEATURE:
<221> NAME/KEY: CD
<222> LOCATION: (13)..(450)
<220> FEATURE:
<221> NAME/KEY: Linker
<222> LOCATION: (451)..(487)
<220> FEATURE:
<221> NAME/KEY: CBD
<222> LOCATION: (488)..(595)

<400> SEQUENCE: 2
```

Ser Pro Leu Pro Gln Gln Gln Arg Tyr Gly Lys Arg Ala Thr Ser Asp
 1               5                  10                  15

Asp Trp Lys Gly Lys Ala Ile Tyr Gln Leu Leu Thr Asp Arg Phe Gly
             20                  25                  30

Arg Ala Asp Asp Ser Thr Ser Asn Cys Ser Asn Leu Ser Asn Tyr Cys
         35                  40                  45

Gly Gly Thr Tyr Glu Gly Ile Thr Lys His Leu Asp Tyr Ile Ser Gly
     50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                 85                  90                  95

Asn Phe Gly Asp Glu Ser Gln Leu Lys Ala Leu Ile Gln Ala Ala His
            100                 105                 110

Glu Arg Asp Met Tyr Val Met Leu Asp Val Val Ala Asn His Ala Gly
        115                 120                 125

Pro Thr Ser Asn Gly Tyr Ser Gly Tyr Thr Phe Gly Asp Ala Ser Leu
    130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
            180                 185                 190

Tyr Ser Phe Asp Gly Ile Arg Ile Asp Thr Val Lys His Ile Arg Lys
        195                 200                 205

Asp Phe Trp Thr Gly Tyr Ala Glu Ala Ala Gly Val Phe Ala Thr Gly
    210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
            260                 265                 270

Ser Asn Arg Asn Ala Phe Glu Asp Thr Ser Val Leu Thr Thr Phe Val
        275                 280                 285

Asp Asn His Asp Asn Pro Arg Phe Leu Asn Ser Gln Ser Asp Lys Ala
    290                 295                 300

Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro

```
                     325                 330                 335
Ala Asn Arg Glu Val Leu Trp Thr Thr Asn Tyr Asp Thr Ser Ser Asp
            340                 345                 350

Leu Tyr Gln Phe Ile Lys Thr Val Asn Ser Val Arg Met Lys Ser Asn
            355                 360                 365

Lys Ala Val Tyr Met Asp Ile Tyr Val Gly Asp Asn Ala Tyr Ala Phe
            370                 375                 380

Lys His Gly Asp Ala Leu Val Val Leu Asn Asn Tyr Gly Ser Gly Ser
385                 390                 395                 400

Thr Asn Gln Val Ser Phe Ser Val Ser Gly Lys Phe Asp Ser Gly Ala
                405                 410                 415

Ser Leu Met Asp Ile Val Ser Asn Ile Thr Thr Val Ser Ser Asp
                420                 425                 430

Gly Thr Val Thr Phe Asn Leu Lys Asp Gly Leu Pro Ala Ile Phe Thr
            435                 440                 445

Ser Ala Thr Gly Gly Thr Thr Thr Thr Ala Thr Pro Thr Gly Ser Gly
            450                 455                 460

Ser Val Thr Ser Thr Ser Lys Thr Thr Ala Thr Ala Ser Lys Thr Ser
465                 470                 475                 480

Thr Ser Thr Ser Ser Thr Ser Cys Thr Thr Pro Thr Ala Val Ala Val
                485                 490                 495

Thr Phe Asp Leu Thr Ala Thr Thr Thr Tyr Gly Glu Asn Ile Tyr Leu
                500                 505                 510

Val Gly Ser Ile Ser Gln Leu Gly Asp Trp Glu Thr Ser Asp Gly Ile
            515                 520                 525

Ala Leu Ser Ala Asp Lys Tyr Thr Ser Ser Asp Pro Leu Trp Tyr Val
            530                 535                 540

Thr Val Thr Leu Pro Ala Gly Glu Ser Phe Glu Tyr Lys Phe Ile Arg
545                 550                 555                 560

Ile Glu Ser Asp Asp Ser Val Glu Trp Glu Ser Asp Pro Asn Arg Glu
                565                 570                 575

Tyr Thr Val Pro Gln Ala Cys Gly Thr Ser Thr Ala Thr Val Thr Asp
                580                 585                 590

Thr Trp Arg
        595

<210> SEQ ID NO 3
<211> LENGTH: 574
<212> TYPE: PRT
<213> ORGANISM: Trametes cingulata
<220> FEATURE:
<221> NAME/KEY: mat_peptide
<222> LOCATION: (19)..(574)

<400> SEQUENCE: 3

Met Arg Phe Thr Leu Leu Thr Ser Leu Leu Gly Leu Ala Leu Gly Ala
            -15                 -10                 -5

Phe Ala Gln Ser Ser Ala Ala Asp Ala Tyr Val Ala Ser Glu Ser Pro
 -1   1                  5                  10

Ile Ala Lys Ala Gly Val Leu Ala Asn Ile Gly Pro Ser Gly Ser Lys
15                  20                  25                  30

Ser Asn Gly Ala Lys Ala Gly Ile Val Ile Ala Ser Pro Ser Thr Ser
                35                  40                  45

Asn Pro Asn Tyr Leu Tyr Thr Trp Thr Arg Asp Ser Ser Leu Val Phe
            50                  55                  60

Lys Ala Leu Ile Asp Gln Phe Thr Thr Gly Glu Asp Thr Ser Leu Arg
```

```
                65                  70                  75
Thr Leu Ile Asp Glu Phe Thr Ser Ala Glu Ala Ile Leu Gln Gln Val
 80                  85                  90

Pro Asn Pro Ser Gly Thr Val Ser Thr Gly Gly Leu Gly Glu Pro Lys
 95                 100                 105                 110

Phe Asn Ile Asp Glu Thr Ala Phe Thr Asp Ala Trp Gly Arg Pro Gln
                    115                 120                 125

Arg Asp Gly Pro Ala Leu Arg Ala Thr Ala Ile Ile Thr Tyr Ala Asn
                130                 135                 140

Trp Leu Leu Asp Asn Lys Asn Thr Thr Tyr Val Thr Asn Thr Leu Trp
                145                 150                 155

Pro Ile Ile Lys Leu Asp Leu Asp Tyr Val Ala Ser Asn Trp Asn Gln
                160                 165                 170

Ser Thr Phe Asp Leu Trp Glu Glu Ile Asn Ser Ser Phe Phe Thr
175                 180                 185                 190

Thr Ala Val Gln His Arg Ala Leu Arg Glu Gly Ala Thr Phe Ala Asn
                195                 200                 205

Arg Ile Gly Gln Thr Ser Val Val Ser Gly Tyr Thr Thr Gln Ala Asn
                210                 215                 220

Asn Leu Leu Cys Phe Leu Gln Ser Tyr Trp Asn Pro Thr Gly Gly Tyr
                225                 230                 235

Ile Thr Ala Asn Thr Gly Gly Arg Ser Gly Lys Asp Ala Asn Thr
                240                 245                 250

Val Leu Thr Ser Ile His Thr Phe Asp Pro Ala Ala Gly Cys Asp Ala
255                 260                 265                 270

Val Thr Phe Gln Pro Cys Ser Asp Lys Ala Leu Ser Asn Leu Lys Val
                275                 280                 285

Tyr Val Asp Ala Phe Arg Ser Ile Tyr Ser Ile Asn Ser Gly Ile Ala
                290                 295                 300

Ser Asn Ala Ala Val Ala Thr Gly Arg Tyr Pro Glu Asp Ser Tyr Met
                305                 310                 315

Gly Gly Asn Pro Trp Tyr Leu Thr Thr Ser Ala Val Ala Glu Gln Leu
320                 325                 330

Tyr Asp Ala Leu Ile Val Trp Asn Lys Leu Gly Ala Leu Asn Val Thr
335                 340                 345                 350

Ser Thr Ser Leu Pro Phe Phe Gln Gln Phe Ser Ser Gly Val Thr Val
                355                 360                 365

Gly Thr Tyr Ala Ser Ser Ser Thr Phe Lys Thr Leu Thr Ser Ala
                370                 375                 380

Ile Lys Thr Phe Ala Asp Gly Phe Leu Ala Val Asn Ala Lys Tyr Thr
                385                 390                 395

Pro Ser Asn Gly Gly Leu Ala Glu Gln Tyr Ser Arg Ser Asn Gly Ser
                400                 405                 410

Pro Val Ser Ala Val Asp Leu Thr Trp Ser Tyr Ala Ala Ala Leu Thr
415                 420                 425                 430

Ser Phe Ala Ala Arg Ser Gly Lys Thr Tyr Ala Ser Trp Gly Ala Ala
                435                 440                 445

Gly Leu Thr Val Pro Thr Thr Cys Ser Gly Ser Gly Gly Ala Gly Thr
                450                 455                 460

Val Ala Val Thr Phe Asn Val Gln Ala Thr Thr Val Phe Gly Glu Asn
                465                 470                 475

Ile Tyr Ile Thr Gly Ser Val Pro Ala Leu Gln Asn Trp Ser Pro Asp
480                 485                 490
```

```
Asn Ala Leu Ile Leu Ser Ala Ala Asn Tyr Pro Thr Trp Ser Ile Thr
495                 500                 505                 510

Val Asn Leu Pro Ala Ser Thr Thr Ile Glu Tyr Lys Tyr Ile Arg Lys
                515                 520                 525

Phe Asn Gly Ala Val Thr Trp Glu Ser Asp Pro Asn Asn Ser Ile Thr
            530                 535                 540

Thr Pro Ala Ser Gly Thr Phe Thr Gln Asn Asp Thr Trp Arg
        545                 550                 555
```